(12) United States Patent
Radko (10) Patent No.: US 6,230,708 B1
(45) Date of Patent: May 15, 2001

(54) VENTILATOR TRIGGERING DEVICE

(75) Inventor: John Radko, Irvine, CA (US)

(73) Assignee: Sechrist Industries, Inc., Anaheim, CA (US)

( * ) Notice: Subject to any disclaimer, the term of this patent is extended or adjusted under 35 U.S.C. 154(b) by 0 days.

(21) Appl. No.: 09/183,761

(22) Filed: Oct. 30, 1998

(51) Int. Cl.[7] ..................................................... A62B 9/02
(52) U.S. Cl. ................................ 128/205.24; 128/200.24; 128/204.18
(58) Field of Search ......................... 128/204.18, 204.26, 128/205.24, 207.14, 207.16, 200.24

(56) References Cited

U.S. PATENT DOCUMENTS

| | | | |
|---|---|---|---|
| 4,538,607 | * | 9/1985 | Saul .................................. 128/207.16 |
| 4,582,058 | * | 4/1986 | Depel et al. ...................... 128/207.17 |
| 5,042,473 | * | 8/1991 | Lewis ................................ 128/205.24 |
| 5,059,208 | * | 10/1991 | Coe et al. ................................. 623/9 |
| 5,390,666 | | 2/1995 | Kimm et al. . |
| 5,501,214 | * | 3/1996 | Sabo ................................. 128/205.24 |
| 5,513,631 | | 5/1996 | McWilliams . |
| 5,542,415 | | 8/1996 | Brody . |
| 5,542,447 | * | 8/1996 | Foote et al. ........................... 137/113 |
| 5,660,171 | | 8/1997 | Kimm et al. . |

* cited by examiner

Primary Examiner—Glenn K. Dawson (57) ABSTRACT

An improved device for providing a patient triggered breath to a patient including a ventilator having one tube that supplies a flow of a gas and another tube that delivers gas to an exhalation valve, an endo-tracheal tube that is in communication with the lungs of the patient, and a connector for connecting the supply tube from the ventilator to the endo-trachael tube. The connector has a chamber and a two-way check valve, the two-way check valve having an inhalation check valve and an exhalation check valve. The wall of the connector may further include an opening for connection to a pressure transducer. The volume of the chamber of the connector is between about 1.0 cm$^3$ to 1.3 cm$^3$ and the exhalation valve is selectively moved from its opened position to its closed position when the pressure transducer senses a reduction in pressure within the chamber of between about 0.25 cm of water and 2.0 cm of water and wherein the exhalation valve is moved from its closed position to it opened position after a predetermined amount of time.

18 Claims, 6 Drawing Sheets

FIG. 1
PRIOR ART
(INHALATION STAGE)

FIG. 2 (EXHALATION)

VENTILATOR TRIGGERING DEVICE

FIELD OF THE INVENTION

This invention relates in general to ventilators used to assist a patient in breathing, and more particularly to an improved apparatus and method for use in detecting the initiation of a patient effort breath and triggering the ventilator to provide a patient assist breath that is synchronized to the breath of the patient.

BACKGROUND OF THE INVENTION

Patients of many different ailments often suffer from weaknesses or other inabilities to obtain a sufficient oxygen supply under their own power. In many cases, the patient cannot breath at all on their own and can only survive with the assistance of a ventilator. In other cases, the patient is able to breath on their own, but the energy expended by the patient in breathing could sap the patient of the energy needed to properly heal their ailments. In this case, the patient will benefit greatly from the use of a ventilator to assist the patient in their breathing by providing oxygen supplied from a ventilator.

The use of ventilators for patients having difficulty breathing is well-known. One type of ventilator that is commonly used is known as a positive-pressure ventilator. The positive-pressure ventilator forces the needed air, pure oxygen, or other gas mixture needed by the patient into the patient's lungs under an external pressure created by the ventilator. The ventilator forces the gases into the patient through an endo-tracheal tube, which may be placed through the patient's mouth or nose and directly into the patient's trachea. The ventilator can be adjusted to provide the patient with the proper mixture of gases, at the proper temperature, and a predetermined interval.

Such ventilators are configured to allow the patient to exhale only at predetermined times. Thus, when the machine determines that the patient should exhale, an exhalation valve is opened. The patient's lungs, acting against the reduced pressure in the system caused by the opening of the exhalation valve, force the gases out of the lungs and through the exhalation valve to the ambient atmosphere. After a predetermined time, the ventilator closes the exhalation valve, and the pressure build-up caused by the gas flowing from the ventilator fills the patient's lungs. Again, after the predetermined time described above, the exhalation valve is opened and the patient is permitted to exhale.

Such positive-pressure ventilators are useful for patients who cannot breath at all under their own power. Such ventilators may present difficulties, however, for use with patients who are capable of breathing or attempting to breathe under their own power, which is referred to herein as patient effort breathing. For instance, when a patient takes a spontaneous breath while under a positive-pressure ventilator, and the ventilator is not synchronized to the patient's breathing patterns, the ventilator may be forcing air into the patient's lungs while the patient is attempting to force air out of their lungs on their own. In these cases, the ventilator may actually cause unintended harm to the patient.

Ventilators have been developed which synchronize the ventilator's assistance to the patient's natural breathing pattern. These ventilators attempt to accurately determine the initiation of the patient effort breathing and, as quickly as possible, deliver a patient triggered breath, i.e., a breath delivered by a ventilator upon detection of the initiation of a patient effort breath. It is very important in these cases that the sensor sense the initiation of the patient effort breath as soon as possible and report this event via a trigger signal to the ventilator, so that the ventilator can properly provide the external pressure to assist the patient's breath, and not exert the external pressure while the patient exhales.

Numerous types of sensors are known in the art for sensing the initiation of a patient effort breath and triggering a signal to the ventilator. One type of sensor, shown in U.S. Pat. No. 5,513,631 to McWilliams, attaches to the external surface of the nose of the patient. The sensor is a pneumatic device that senses movement by compression of a constant-volume envelope. Movements from the patient's nose that occur as a result of the alae nasi reflex, which occur even prior to the diaphragm movement of the patient prior to a breath, are sensed by the pneumatic device and transmitted to the ventilator. While this device is adequate for its intended purpose, this device may not be entirely accurate under all conditions and in fact it may even be triggered by movements of the nose other than prior to a breath. It may also not provide a signal as soon as possible when the patient makes a patient effort breath.

U.S. Pat. No. 5,542,415 to Brody discloses a sensor for a ventilator for patient-assisted breathing. The sensor is taped to the abdomen of the patient and produces an output signal that is indicative of the movement of the diaphragm of the patient. The rate of change of the output signal with time is determined. When the rate of change with time exceeds a preselected value, a ventilation of the lungs of the patient by an external ventilator is initiated. While this device is adequate for its intended purpose, this device may not be entirely accurate under all conditions and in fact it may even be triggered by movements of the abdomen other than to take a breath.

Patient-assisted ventilators that sense the initiation of a patient effort breath by sensing changes in the flow rate of the gas being provided by the ventilator caused by the initiation of a patient effort breath are also known. For instance, U.S. Pat. Nos. 5,660,171 and 5,390,666 to Kimm et. al. disclose a system and method for flow triggering of pressure supported ventilation by comparison of inhalation and exhalation flow rates. The system provides a continuous flow of gas to the patient and provides additional gas to the patient when the system senses, by differences in flow rates, the patient's inhalation. The system utilizes a number of flow meters 16, 18, 32, 41, 42, and 43 to sense the rate of flow of gas through the system and utilizes two proportional solenoid valves 20 and 22 for controlling the flow of the air to and from the patient. While this device is adequate for its intended purpose, there is room to improve the device by eliminating the numerous flow meters thereby making the device less expensive to manufacture and more responsive to the patient's breathing. The flow meters may be prohibitively expensive, because there is a significant cost for each flow meter, and, in some cases, they must be changed for each patient. Further, ventilators often humidify the air and the patient's exhaled gases have 100% humidity. Thus there often is condensation around the flow meter, which may adversely effect the measurement of the flow of the gases.

Another method known for the detection of the initiation of a patient assist breath is the measurement of the change in pressure of the gases at the initation of a patient effort breath. There is known a pressure trigger device developed at the Massachusetts Institute of Technology that detects such changes in pressure. (See FIG. 1). The MIT ventilator trigger device employs a y-shaped connector having two separate check valves, an inhalation check valve, and an exhalation check valve, each located on a separate portion of the y-shaped connector. The configuration of the check valves provides a relatively small volume, approximately 10 cm³, separate from the rest of the relatively voluminous, approximately 600 cm³ of the patient circuit (the tubing to and from the patient and the ventilator). When the patient initiates a patient effort breath, the patient's lungs expand, thereby increasing the volume of the space between the patient's lungs and the check valves, and thereby lowering the pressure within this space. An opening in the wall of this chamber with a connection to a pressure transducer can measure this change in pressure and send a signal to the ventilator that the patient is making a patient assist breath.

The change in pressure caused by the patient assist breath is sufficient to overcome the cracking pressure of the inhalation check valve, thereby allowing the gases flowing from the ventilator to flow through the check valve through the connector, through the endo-tracheal tube, and into the patient's lungs. After a predetermined time, an exhalation valve is opened, which releases the pressure of the gas flowing to the patient, thereby closing the inhalation check valve. With the pressure to the patient's lungs reduced, the lungs compress to their resting state and the patient exhales. The increased pressure within the chamber of the connector against the exhalation check valve is sufficient to overcome the cracking pressure of the exhalation check valve, thereby opening the exhalation check valve and permitting the patient's exhalation gas to escape through the exhalation check valve and out the exhalation valve to the ambient atmosphere. Once the patient has exhaled, the pressure against the exhalation check valve is reduced and the exhalation check valve will close. The process can then begin again with the patient effort breath.

While the MIT ventilator trigger device is adequate for its intended purpose, it can be improved. For instance, the volume of the chamber of the MIT device, being about 10 cm³ is relatively large, thereby requiring rather large changes in pressure to cause the pressure sensor to react. In other words, the relatively large chamber reduces the sensitivity of the device to pressure changes caused by the initiation of the patient effort breath and may even cause the patient to exert additional force while attempting to breath before the sensor will sense the patient's breath. Thus, the strength of the patient effort breath may have to be relatively large to create a sufficient drop in pressure to be sensed by the pressure transducer.

Further, the relatively large volume creates the additional problem that the amount of exhaled gas from the patient may not be completely removed from the chamber when the exhalation check valve closes. Thus, there may be an unacceptable quality of gas exchange to the patient, with the possibility occurring that the patient may actually inhale up to 10 cm³ of exhaled gas. This may be a real concern with premature babies who have a tidal volume of between 8–10 cm³.

Accordingly, it will be appreciated from the foregoing that there is a definite need for an improved ventilator trigger device that has a greater sensitivity to changes in pressure caused by the initiation of a patient effort breath. The improved ventilator trigger device should be inexpensive to manufacture and use. It should be responsive to the breathing patterns of the patient and should not be triggered by events other than the initation of a patient effort breath. The improved ventilator trigger device should also have a minimum of moving parts and should be easy to clean and sterilize, or even be disposable.

SUMMARY OF THE INVENTION

The present invention is embodied in an improved method and apparatus for providing a patient triggered breath from a ventilator. The present invention provides an improved ability to detect the initiation of a patient effort breath and improved rate and quality of gas exchange. The invention resides in a connector for use in a ventilator/patient system. The connector has a wall which defines a chamber and has a two-way check valve which has an inhalation check valve and an exhalation check valve.

The improved ventilator trigger device of the present invention provides a chamber having a small enough volume so that reductions in pressure caused when a patient's lungs begin to expand at the start of a patient effort breath can be quickly and accurately detected and a patient assist breath can be quickly initiated with the gas flow from the ventilator.

The ventilator trigger device of the present invention is part of a larger gas flow circuit that connects a constant gas flow source—a ventilator—to the patient's lungs, through an endo-tracheal tube, and connects the exhalation of the patient to the ambient atmosphere through an exhalation valve.

The ventilator provides a constant flow of gas at a pressure that is insufficient to overcome the cracking pressure of the inhalation check valve. At the moment just prior to the start of the inhalation phase of the patient effort breath, both the inhalation and exhalation check valves are closed and the area within the chamber, endo-tracheal tube, and the patient's lungs is finite. Gas flow from the ventilator travels over the check valves, through a patient wye, and out to the ambient atmosphere through the open exhalation valve.

As the patient begins a patient assist breath, the volume of the patient's lungs begins to increase. This increase in volume of the lungs causes an increase in the overall volume of the chamber/endo-trachael tube/lungs and thus a reduction in the pressure of the gas within the chamber area can be detected by, for instance, a pressure transducer, that is, communication with the interior of the chamber.

When the start of the patient effort breath is detected by the pressure transducer, the pressure transducer sends a signal to the ventilator indicating that the patient has initiated a patient effort breath, and thus that the patient is in need of a patient triggered breath. As a result, the ventilator closes the exhalation valve, thereby causing the pressure with the ventilator tube to increase and overcome the cracking pressure of the inhalation check valve.

As the inhalation check valve opens, the gas flowing from the ventilator is able to flow through the inhalation check valve, through the chamber, through the patient's endo-tracheal tube, and into the patient's lungs—in synchronization with the patient effort breath. The ventilator is set to a predetermined time for the gas to flow to the patient's lungs, and, after this predetermined time, the exhalation valve re-opens, thereby allowing the gas flowing from the ventilator to flow out of the system through the exhalation valve and into the ambient atmosphere.

As the exhalation valve opens, the pressure at the inhalation check valve is reduced to an amount that is less than the cracking pressure of the inhalation check valve, thereby causing the inhalation check valve to close. This reduction of the pressure at the inhalation check valve also causes a reduction in the pressure within the patient's lungs. This reduction of pressure permits the patient's lungs to compress to their resting state. As the patient's lungs compress, the lungs exhale the gas from within. The exhaling gas from the lungs causes an increase in the pressure within the chamber an amount that is greater than the cracking pressure of the exhalation check valve, thereby opening the exhalation check valve and permitting the exhalation gas from the patient's lungs to pass into the patient wye tube and out to the ambient atmosphere through the opened exhalation valve.

When the lungs have exhaled substantially all of the gas, the pressure within the chamber is again reduced and the exhalation check valve can close. The process then starts over again when the patient begins to make a patient assist breath and the pressure within the chamber is again reduced.

Other features and advantages of the present invention will become apparent from a consideration of the following detailed description.

DETAILED DESCRIPTION OF THE PREFERRED EMBODIMENTS

The present invention is embodied in an improved method and apparatus for providing a patient triggered breath from a ventilator. The invention resides in an improved connector in a patient/ventilator system that provides a chamber having a relatively small volume. This relatively small volume of the chamber provides the advantages over other ventilator trigger devices in that it permits a better rate and quality of gas exchange and provides a better sensitivity to pressure changes, thereby providing more accurate, earlier, and faster detection of the initiation of patient effort breathing.

The present invention includes a connector 10 for connecting a patient's endo-tracheal tube 12 with a tube 14 emanating from the ventilator 16 itself and with a tube 18 that is in selective communication with the ambient atmosphere 20. (See FIGS. 2, 3, 4, and 5). It should be understood that the accompanying drawings are merely exemplary of the inventive concept herein and are therefore not production drawings, nor are they necessarily drawn to scale.

The connector 10 has a chamber 22 and has at least one wall 24, which forms part of the chamber 22. The chamber 22 is defined by the wall or walls 24 of the connector 10 and by the bottom of the two-way check valve 26, described below, and the plane that intersects the bottom edge of the connector 28. The chamber 22 of the connector 10 of the present invention preferably has a volume of between about 1.0 to 1.3 cm$^3$. The connector 10 also has a first and second opening 30 and 32, respectively, for the passage of gases. The openings 30 and 32 may be cylindrical and sized to fit the openings of an endo-tracheal tube 12 and a patient wye tube 34, as are well-known to those of ordinary skill in the art. The chamber 22 of the connector 10 may be, but does not necessarily have to be, cylindrical in shape, although the chamber should be of such a shape so as to minimize the volume of space contained within the walls 24 of the chamber 22 and that are inexpensive and simple to manufacture.

The walls 24 of the connector 10 may be formed from any material strong enough to support connection to an endo-tracheal tube 12 and a patient wye tube 34, and are preferably formed from a disposable, non-autoclavable material, such as ABS plastic. It is preferred that the material be disposable and non-autoclavable for safety reasons—so that each patient to use the ventilator be given their own connector to reduce the possibility of the transmission of germs or viruses that often are contained in the breath of patients who use ventilators and which sometimes may not be removed by the use of an autoclave. It is also preferred that the walls 24 of the connector 10 be transparent so that the interior of the chamber 22 can be viewed to determine whether there is any foreign matter contained within the chamber 22 that could block the passage of gasses through the chamber 22.

Figure 2:
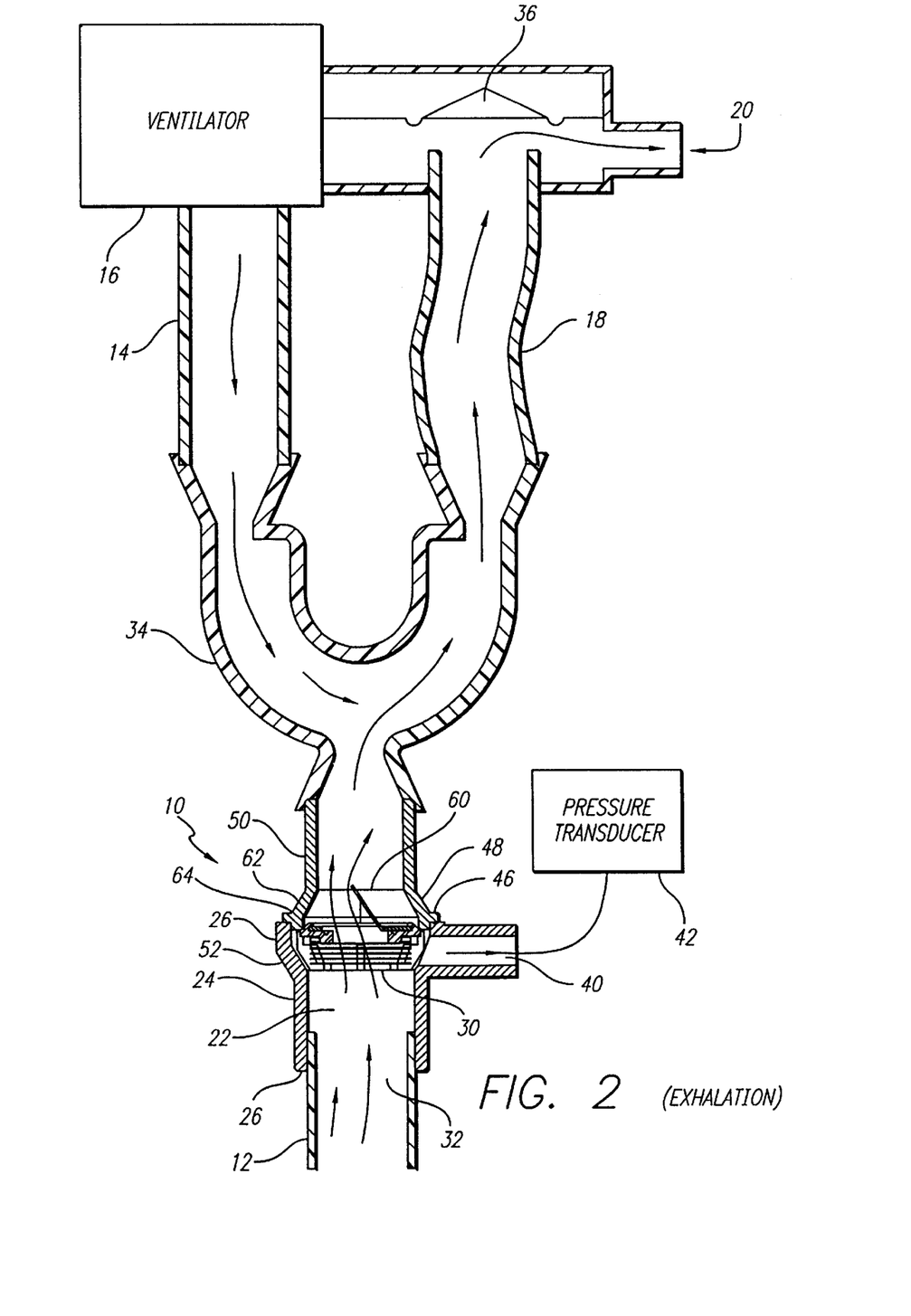
FIG. 2 is a side cross-sectional view of an embodiment of the improved ventilator trigger device of the present invention showing the system during the exhalation phase.
Figure 3:
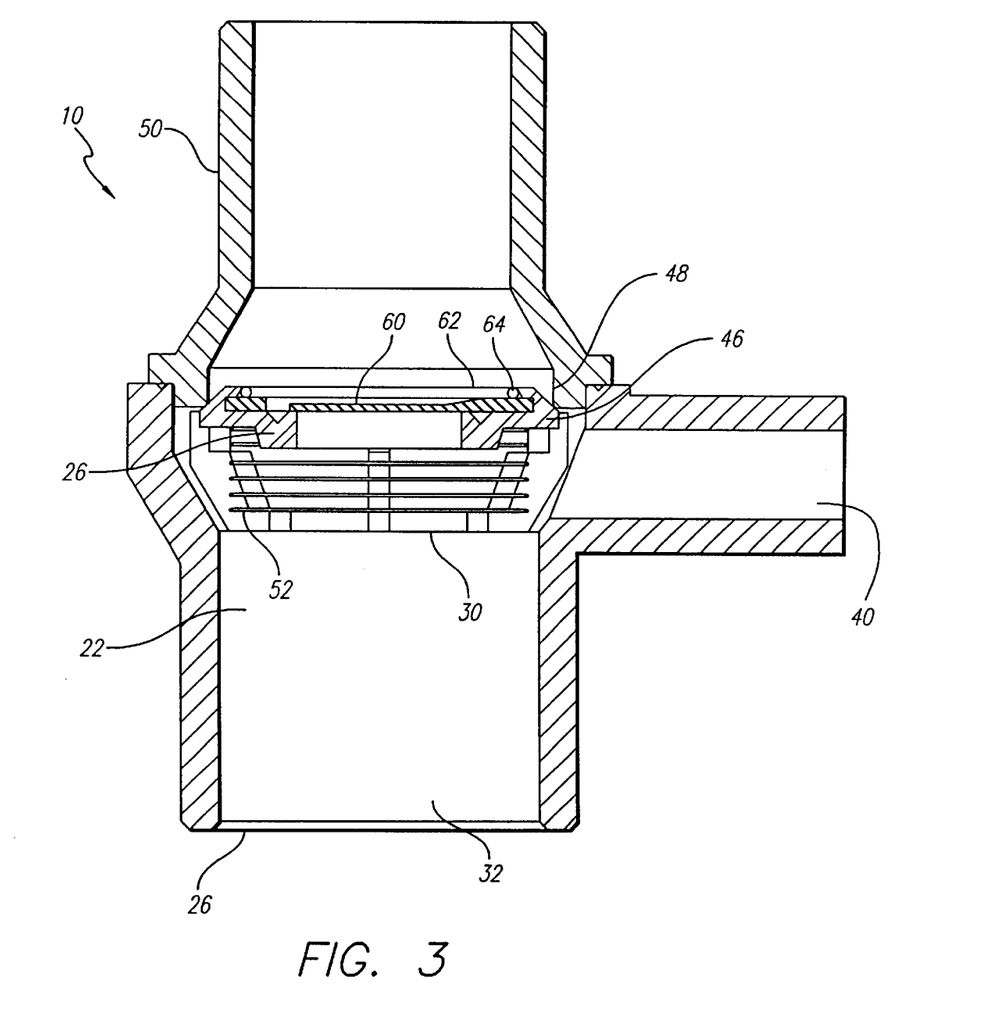
FIG. 3 is a side cross-sectional view of an embodiment of the improved ventilator trigger device of the present invention.
Figure 4:
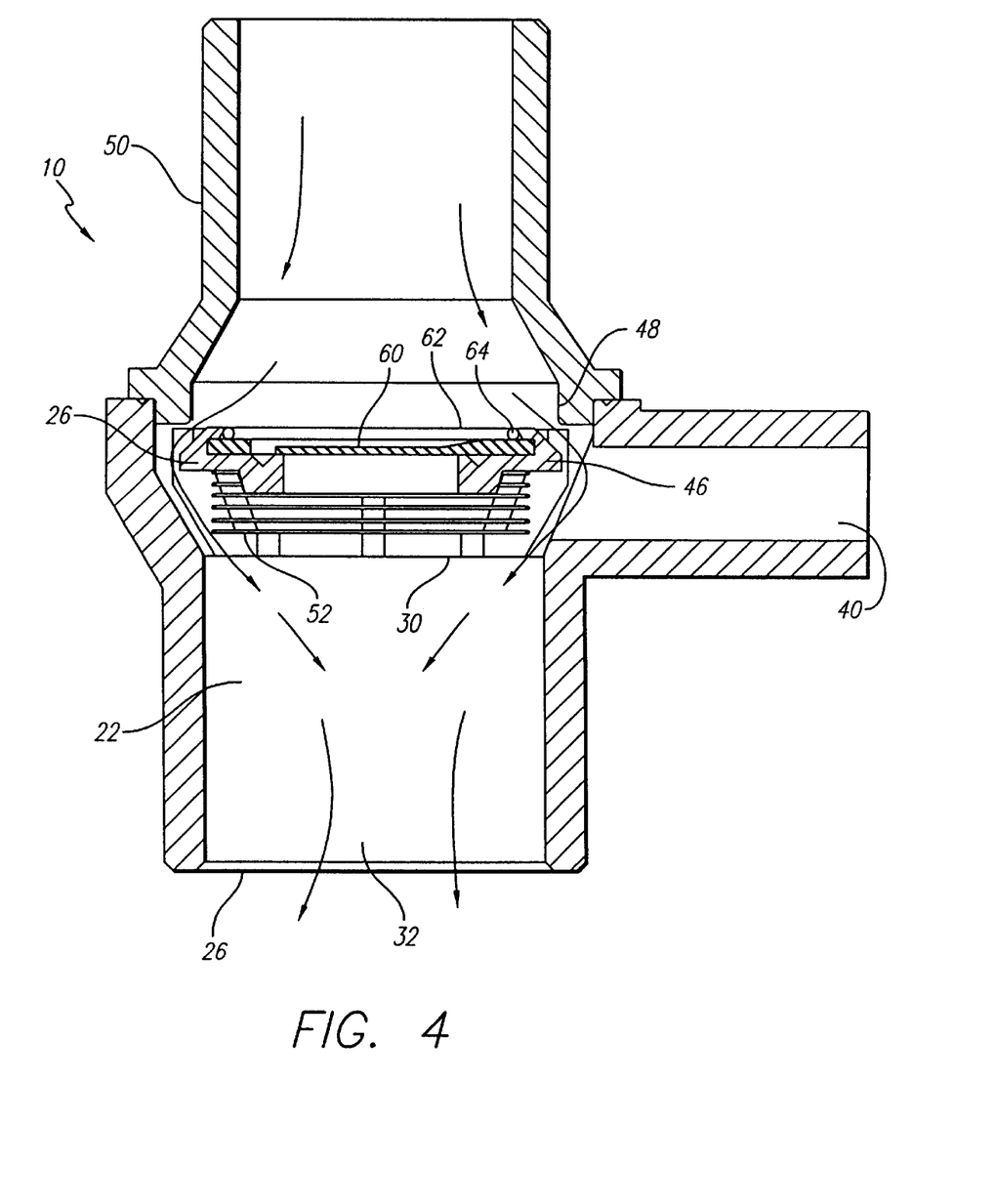
FIG. 4 is a side cross-sectional view of the ventilator trigger device of FIG. 3 during the inhalation phase.
Figure 5:
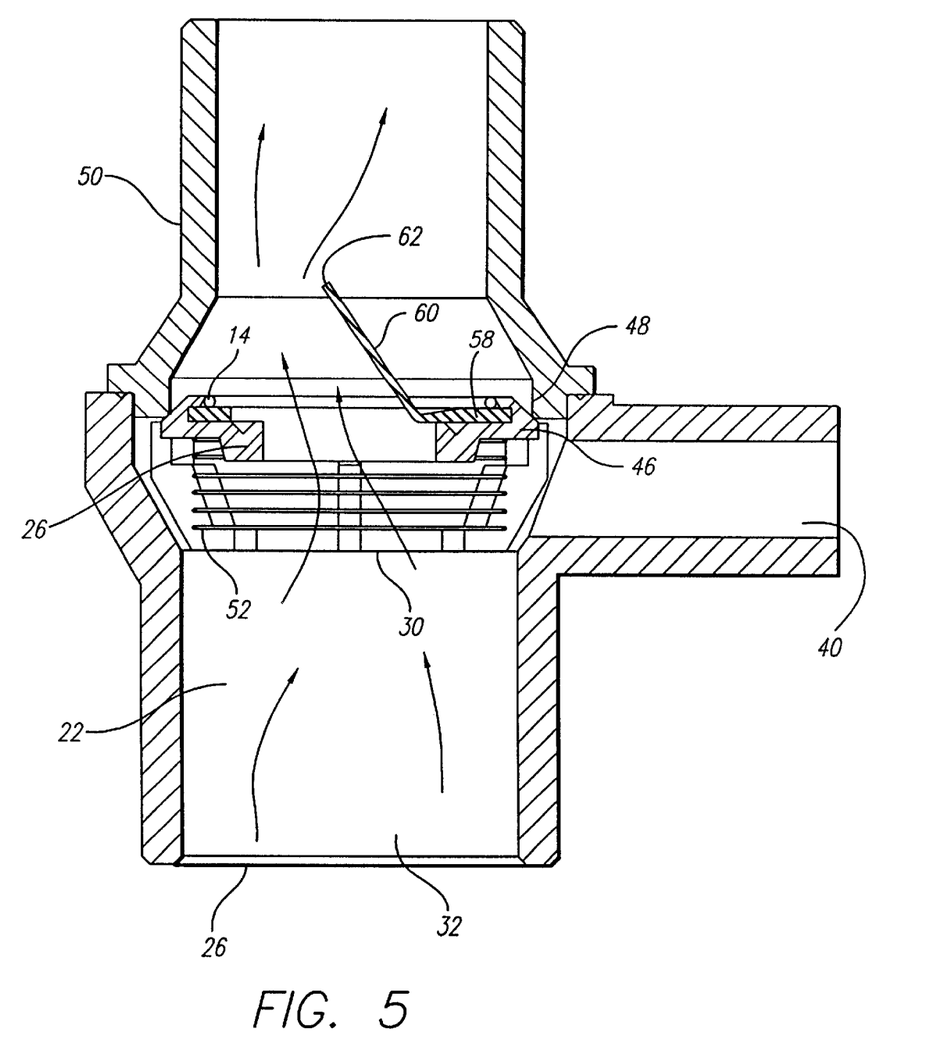
FIG. 5 is a side cross-sectional view of the ventilator trigger device of FIG. 3 during the exhalation phase.

As shown in FIG. 2, the connector of the present invention is part of a larger gas flow circuit that connects a constant gas flow source—a ventilator 16—to the patient's lungs, through an endo-tracheal tube 12, and connects the exhalation of the patient to the ambient atmosphere 20 through an exhalation valve 36. The system is formed from tubes 14 and 18, as is known in the art, the tubes being formed from any plastic or other material commonly used for such tubes. The endo-trachael tube 12 is also any endo-tracheal tube, as is also well-known in the art.

The ventilator 16 provides an output of a constant flow of air, pure oxygen, or any other gas, or gas mixture, that is needed to be transmitted to the patient. The ventilator may be an electro-pneumatic, continuous flow, time cycled, pressure-limited ventilator for infant, pediatric, and/or adult patients. The ventilator may be adjusted in terms of numerous variables, including respiratory rate, inspiratory time, trigger sensitivity, inspiratory and expiratory pressure, waveform, $FiO_2$, flow rate, etc. and may display these variables and data to the user or health care provider. The gases from the ventilator 16 may also pass through a humidifier before entering the patient's lungs, if there is a need to add humidity to the gases. The ventilator 16 preferably provides a constant flow of gas at a rate of between about 2 to 12 liters per minute, if the patient is an infant, or between 16 to 32 liters per minute if the patient is an adult. The ventilator provides a constant flow of gas at a pressure of 0 to 80 cm of water, which, when the exhalation valve 36 is open, is insufficient to overcome the cracking pressure of the inhalation check valve 38, as discussed below.

The connector 10 may also have an opening 40 in a portion of its walls 24 for the attachment of a tube (not shown) which permits the gases of the chamber 22 to communicate with a pressure transducer 42 located at the other end of the tube. The pressure transducer 42 is preferably any transducer that is capable of reading changes of pressure in the magnitude of as low as about 0.25 cm of water to 2 cm of water.

Located within the connector 10 is a two-way check valve 26, which sits just above the chamber 22. (FIGS. 2, 3, 4, and 5). The two-way check valve 26 comprises an inhalation check valve 38 and an exhalation check valve 44. The inhalation check valve 38 allows gas to pass from the ventilator 16 and through an opening between the valve 38 and the housing wall 50 in the inhalation check valve 38, and to the patient's lungs. (See FIG. 4). The inhalation check valve 38 is comprised of a plug 46 that is pressed against the interior 48 of the walls 50 of the connector 10 to form an airtight seal sealing the opening between the space above and below the plug 46. The plug is pressed against the walls 50 of the connector 40 by the force of a spring 52 or other similar device. The plug 46 is preferably formed from any type of plastic or similar material, including medical grade silicon, mylar, polyurethane, elastomers, and other similar polymers.

The inhalation valve 38 has a cracking pressure, i.e., the pressure necessary to overcome the force of the spring 52 and cause the plug 46 to be moved towards the spring 52, of approximately 2 to 2.5 cm of water. (FIG. 4) Thus, when the pressure of the gas on the ventilator 16 side of the plug 46 is 2 cm of water or greater than the pressure of the gas on the chamber 22 side of the plug 46, then the plug 46 is forced to move against the force of the spring 52. The walls 50 of the connector 10 are shaped so that, when the plug 46 of the inhalation valve 38 is moved towards the spring 52 the edges of the plug 46 no longer contact the wall 50 of the connector 10, an opening 54 is formed through which gas can flow from the ventilator 16, past the inhalation check valve 38, through the chamber 22, through the endo-trachael tube 12 and into the patient's lungs.

Figure 6:
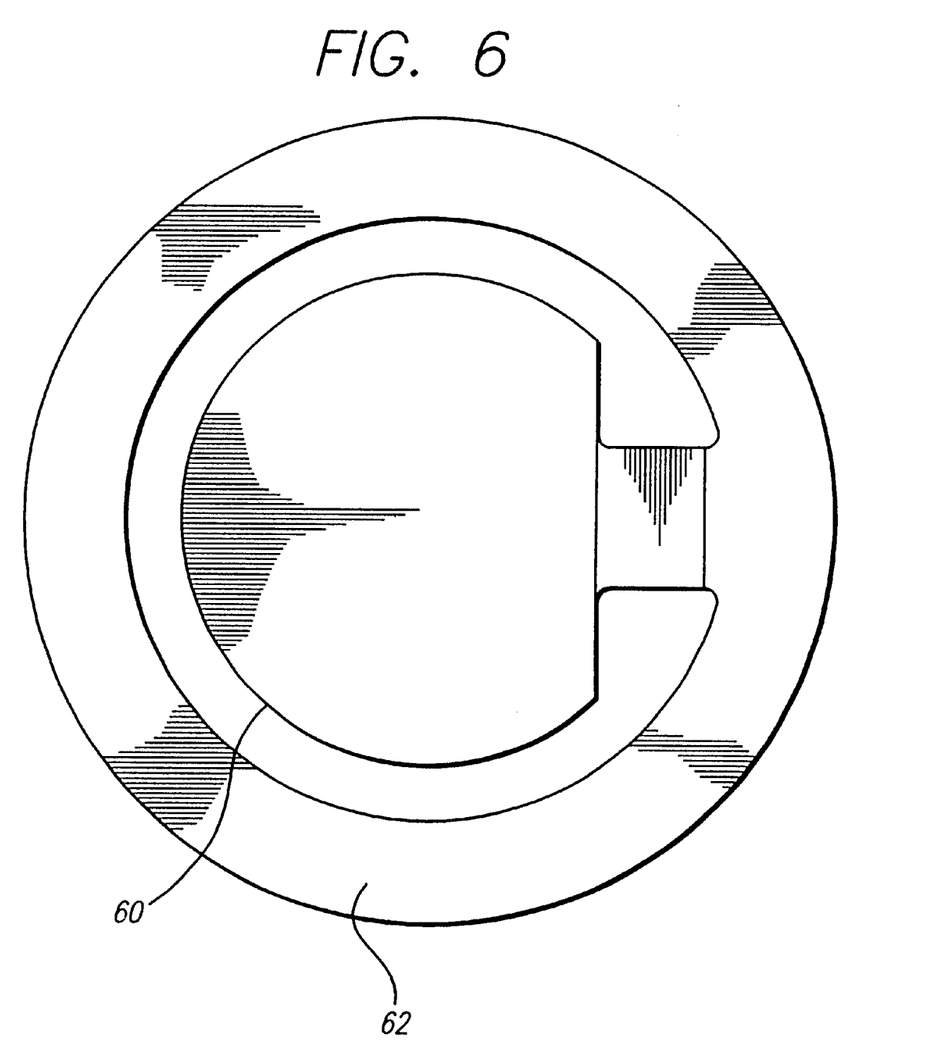
FIG. 6 is a top view of the exhalation check valve in its closed position.

The exhalation check valve 44 allows gas to pass from the patient's lungs, through the exhalation check valve 44, and to the ventilator 16. (See FIGS. 5 and 6). The exhalation check valve 44 is located over an opening 56 formed in the center of the plug 46 of the inhalation valve 38. The exhalation check valve 44 is preferably formed from a piece of medical grade silicone, mylar, polyurethane, elastomers, or other similar polymer, that is shaped with an outer portion of a ring 58 attached to a substantially circular flap 60. The outer portion preferably lies entirely on top of the plug 46 of the of the inhalation check valve 38, whereas only the outer edge 62 of the substantially circular flap 60 lies over the plug 46, with the remainder of the inner portion of the flap 60 covering the opening 56 of the plug 46. The exhalation check valve 44 is maintained in its position on the surface of the plug 46 of the inhalation check valve 38 by the use of a retainer ring 64 that fits over the outer ring portion 58 of the exhalation check valve and, under a portion of the plug 46.

The exhalation check valve 44 has a cracking pressure, i.e., the pressure necessary to overcome the force necessary to lift the flap 60 and expose a portion of the opening 56 of the plug 46 of approximately 2 to 2.5 cm of water. (See FIGS. 5 and 6). Thus, when the pressure of the gas on the patient side of the plug 46 is 2 cm of water or greater than the pressure of the gas on the ventilator 12 side of the plug 46, then the flap 60 is forced upwards to allow gases to pass through the opening of the plug 46 of the inhalation check valve 38 toward the exhalation check valve 44 and to the ambient atmosphere 20.

The present invention provides the benefits of being able to detect the initiation of the patient effort breath quickly— within the first 0.25 to 2 cm of water change in pressure in the chamber 22 of the connector 10, which is within the first 1 to 1.5 cm$^3$ of change in volume of the patient's lungs. The detection of the initiation of the patient effort breath provides the benefit that the ventilator 16 can more accurately and quickly provide the patient with the patient triggered breath from the ventilator. Further, such early detection prevents the patient from having to exert too great an effort to initiate a breath prior to the initiation of the patient triggered breath. With such a reduction in effort by the patient, the patient's energy can be used more appropriately for the healing of the patient's ailments.

The present invention detects the initiation of the patient breath and provides the patient triggered breath as follows. Assuming that the patient has just completed her exhalation phase of a prior breath, and is about to begin the inhalation phase of her breath, the state of the system is such that both the inhalation and exhalation check valves 38 and 44, are closed and the area within the chamber 10, endo-trachael tube 12, and the patient's lungs is finite. (See FIG. 3). The gas flow from the ventilator 12 travels over the two-way check valve 26, through the patient wye 34, and out to the ambient atmosphere 20 through the open exhalation valve 36.

As the patient begins a patient effort breath, the volume of the patient's lungs begins to increase. This increase in volume of the lungs causes an increase in the overall volume of the chamber 22/endo-trachael tube 12/lungs and thereby causing a reduction in the pressure of the gas within the chamber area. (See FIG. 4). This reduction in pressure can be detected by the pressure transducer 42. The pressure transducer 42 is connected to a microprocessor having analog and digital filters, as is known in the art, for filtering out the noise of the gas system and the electronics. The microprocessor is looking for a reduction in the pressure of 0.25 to 2 cm of water within the chamber, with the assumption that there is approximately 0.1 cm of water of noise within the system. The microprocessor is pre-programmed to assume that a reduction in pressure in the chamber, as measured by the pressure transducer, and after filtering, is a sign that the patient has initiated a patient effort breath.

When the start of the patient effort breath is detected by the pressure transducer 42 and the microprocessor, a signal is sent to the ventilator 16 indicating that the patient has initiated a patient effort breath, and thus that the patient is in need of a patient triggered breath. As a result, the ventilator 16 closes the exhalation valve 36. (See, e.g., FIG. 1) The exhalation valve 36 is any valve that can be opened and shut with an electric signal. The exhalation valve 36 opens to the ambient atmosphere 20 and permits the gases flowing within the system to be removed from the system and into the ambient atmosphere.

The closing of the exhalation valve 36 causes the gases flowing within the system to stay within the system and not bleed out into the ambient atmosphere 20 through the exhalation valve 36. As the flowing gases must remain within the system, the pressure with the ventilator tubes 14 and 18 increases. As the pressure increases, the cracking pressure of the inhalation check valve 38 is surpassed and the inhalation check valve 38 is caused to open, thereby permitting the flow of the fresh gases from the ventilator 16 to flow through the inhalation check valve 38, into the chamber 22, through the endo-tracheal tube 12 and into the lungs of the patient. (See FIG. 4).

The quick and early detection of the initiation of the patient effort breath allows the flow of the gas from the ventilator to occur at a time just after the patient has initiated the patient effort breath. In other words, the early detection of the initiation of the patient effort breath and quick opening of the inhalation check valve 38 permit the fresh ventilator gas to be introduced to the lungs of the patient within such a short amount of time that the patient can accurately and assuredly be provided with patient triggered breaths that are properly synchronized with the patient effort breath.

The ventilator 16 is set to a predetermined time for the gas to flow to the patient's lungs. As discussed above, one of the variables that can be adjusted on the ventilator is the inspiratory time. Thus, during this predetermined time, the exhalation valve 36 will remain closed and the gases flowing from the ventilator 16 will pass through the inhalation check valve 38 and into the lungs of the patient. (See FIG. 4). The inspiratory time is preferably between approximately 0.1 to 3.0 seconds. After this predetermined time, the exhalation valve 36 is re-opened, thereby allowing the gas flowing from the ventilator 16 to flow out of the system through the exhalation valve 36 and into the ambient atmosphere 20.

As the exhalation valve 36 opens, the pressure at the inhalation check valve 38 is reduced to an amount that is less than the cracking pressure of the inhalation check valve 38, thereby causing the inhalation check valve 38 to close. This reduction of the pressure at the inhalation check valve 38 also causes a reduction in the pressure within the patient's lungs. This reduction of pressure permits the patient's lungs to compress to their resting state. As the patient's lungs compress, the lungs exhale the gas from within. The exhaling gas from the lungs causes an increase in the pressure within the chamber of an amount that is greater than the cracking pressure of the exhalation check valve 44, thereby opening the exhalation check valve 44 and permitting the exhalation gas from the patient's lungs to pass into the patient wye tube 34 and out to the ambient atmosphere 20 through the opened exhalation valve 36. (See FIG. 2).

When the lungs have exhaled substantially all of the gas, the pressure within the chamber 22 is again reduced and the exhalation check valve 44 can close. The process then starts over again when the patient begins to make a patient assist breath and the pressure within the chamber is again reduced.

Figure 1:
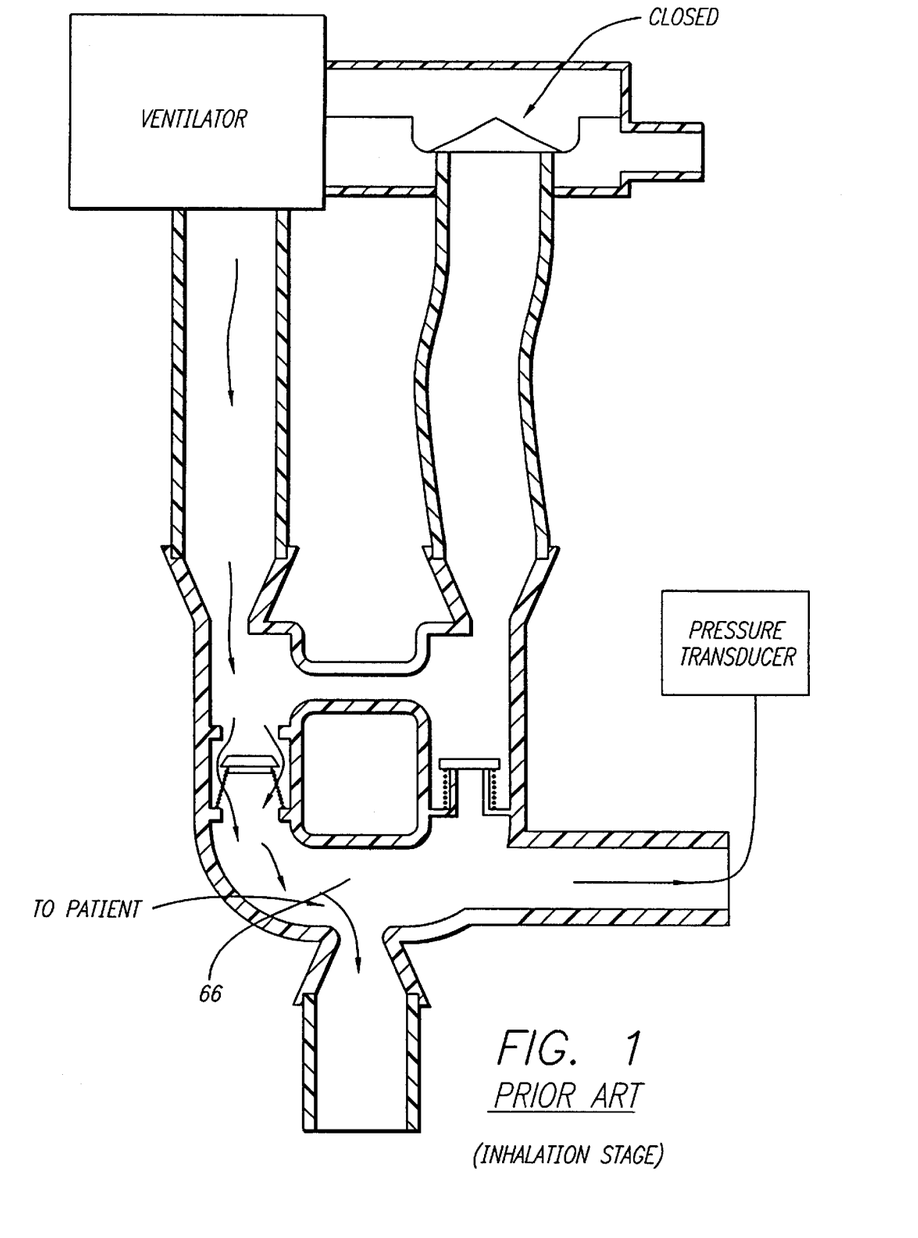
FIG. 1 is a side cross-sectional view of a ventilator system in accordance with a prior art device, showing the system during the inhalation phase.

The use of the two-way check valve 26 with a relatively small-sized chamber 22 results in a faster and greater change in pressure within the chamber when the patient begins a patient effort breath than would occur if the chamber were larger. For instance, the chamber of the present invention can be between about 1.0 to 1.3 cm$^3$, which represents a reduction in the volume of this chamber of one-tenth over the MIT ventilator trigger device. (See FIG. 1). This one-tenth reduction in the volume of the chamber 22 provides the benefit that the change in pressure can be detected ten times faster in the device of the present invention than in the MIT device. (FIG. 1). This is because the change in pressure is due to the change in volume of the patient's lungs as the patient begins their patient effort breath, and because the change in pressure is directly proportional to the change in volume. Thus, the patient effort breath requires less of an effort by the patient for there to be a sufficient change in the pressure to be detected by the pressure transducer.

Further, as the patient exhales and the pressure is reduced within the chamber to a point below the cracking pressure of the exhalation check valve 38, some of the exhaled gases may remain within the chamber 22. Because the volume of the chamber is relatively small, between about 1.0 to 1.3 cm$^3$, only a small amount of the exhaled gases can be returned to the patient's lungs during the initiation of their patient effort breath. Thus, the rate and quality of the gas exchange in the device of the present invention is significantly improved over that of the MIT device. (FIG. 1). For instance, in the present invention, the amount of exhaled gases that could possibly be returned to the patient during their next breath, i.e., the rate of gas exchange in the patient, is at most between about 1.0 to 1.3 cm$^3$ plus the volume of the endo-tracheal tube 12, which is even less.

In the MIT device (FIG. 1), however, the volume of the chamber 66 is about 10 cm$^3$, and thus in the MIT device, the amount of exhaled gases that could possibly be returned to the patient during their next breath can be as much as 10 cm$^3$. (FIG. 1). For an adult who has a tidal volume of 250 cm$^3$ this is an insignificant amount, however, for premature babies, who may have a tidal volume of between about 7 to 10 cm$^3$, they may end up inhaling only exhaled gases.

While a particular form of the invention has been illustrated and described, it will be apparent that various modifications can be made without departing from the scope of the invention. For instance, the inhalation and exhalation check valves 38 and 44 do not have to have the plug 46 and spring 52 and flap 60 configurations described above. Rather, they need only be any type of valve that is capable of maintaining a cracking pressure of between 2.0 to 2.5 cm of water and that are small enough so as to provide a chamber of a small enough volume to provide the benefits described herein. Accordingly, it is not intended that the invention be limited by the specific embodiment disclosed in the drawings and described in detail herein above.

I claim:

1. A connector for connecting a ventilator to a patient, the connector comprising:
   a chamber; and
   a two-way check valve, the two-way check valve having an inhalation check valve and an exhalation check valve wherein the volume of the chamber is between about 1.0 cm$^3$ to 1.3 cm$^3$.

2. The connector of claim 1, wherein the inhalation check valve has a cracking pressure of between about 2 to 2.5 cm of water.

3. The connector of claim 1, wherein the exhalation check valve has a cracking pressure of between about 2 to 2.5 cm of water.

4. The connector of claim 1, wherein the exhalation check valve comprises a flap having a ring shaped-portion and a flap portion.

5. A ventilator trigger device for detecting the initiation of a patient effort breath comprising:
   a chamber having a volume of between about 1.0 cm$^3$ to 1.3 cm$^3$;
   a two-way check valve, the two-way check valve having an inhalation check valve and an exhalation check valve, the cracking pressure of the inhalation check valve being between about 2 to 2.5 cm of water and the cracking pressure of the exhalation check valve being between about 2 to 2.5 cm of water.

6. The ventilator trigger device of claim 5, further including an opening for connection to a pressure transducer.

7. The ventilator trigger device of claim 5, wherein the inhalation check valve comprises a plug having an opening and a spring.

8. The ventilator trigger device of claim 5, wherein the exhalation check valve comprises a flap having a ring shaped-portion and a flap portion.

9. A device for providing a patient triggered breath to a patient's lungs comprising:
   a ventilator having at least one tube that supplies a flow of a gas;
   an endo-tracheal tube that is adapted to be in communication with the lungs of the patient;
   an exhalation valve;
   at least one exhalation tube that is adapted to deliver gas from the patient's lungs to the exhalation valve;
   a connector for connecting the supply tube from the ventilator to the endo-tracheal tube, the connector having a chamber, and having a two-way check valve, the two-way check valve having an inhalation check valve and an exhalation check valve.

10. The device of claim 9, wherein the chamber is defined by at least one wall and wherein said at least one wall further includes an opening for connection to a pressure transducer.

11. The device of claim 10, further including a pressure transducer, wherein the pressure transducer senses changes in pressure within the chamber of the connector.

12. The device of claim 11, wherein the exhalation valve is selectively movable from a closed position to an opened position, and vice versa, and wherein the exhalation valve is moved from its opened position to its closed position when the pressure transducer senses a reduction in pressure within the chamber of between about 0.25 cm of water and 2.0 cm of water and wherein the exhalation valve is moved from its closed position to its opened position after a predetermined amount of time.

13. The device of claim 9, wherein the volume of the chamber of the connector is between about 1.0 cm$^3$ to 1.3 cm$^3$.

14. The device of claim 9, wherein the inhalation check valve has a cracking pressure of between about 2 to 2.5 cm of water.

15. The device of claim 9, wherein the exhalation check valve has a cracking pressure of between about 2 to 2.5 cm of water.

16. The device of claim 9, wherein the inhalation check valve comprises a plug having an opening and a spring.

17. The device of claim 9, wherein the exhalation check valve comprises a flap having a ring shaped-portion and a flap portion.

18. A method for providing a patient with a patient triggered breath from a ventilator comprising:

(1) providing a ventilator having one tube that supplies a flow of a gas and another tube that delivers gas to an open exhalation valve;

(2) providing an endo-tracheal tube that is in communication with the lungs of the patient;

(3) providing a connector for connecting the supply tube from the ventilator to the endo-trachael tube, the connector having a chamber, and having a two-way check valve, the two-way check valve having an inhalation check valve and an exhalation check valve, the exhalation and inhalation check valves being closed prior to the patient initiating a patient effort breath;

(4) sensing a pressure change within the chamber of the connector with a pressure transducer of between about 0.25 cm of water and 2.0 cm of water at the initiation of a patient effort breath;

(5) closing the exhalation valve, thereby causing the inhalation valve to open, thereby causing the gas flowing from the ventilator to enter the endo-tracheal tube;

(6) waiting a predetermined time;

(7) re-opening the exhalation valve after the predetermined time, thereby permitting the gas flowing from the ventilator to be exhausted through the exhalation valve;

(8) waiting as the patient exhales the gas within their lungs, thereby causing the exhalation check valve to open and exhaust the exhaled gases through the opened exhalation valve;

(9) repeating steps 4 through 8.

* * * * *